(12) United States Patent
Lenore et al.

(10) Patent No.: US 12,201,789 B2
(45) Date of Patent: Jan. 21, 2025

(54) VENTRICULOSTOMY PATCH SYSTEM AND METHOD

(71) Applicants: Abbey Lenore, Fair Oaks, CA (US); Alex Nee, Granite Bay, CA (US)

(72) Inventors: Abbey Lenore, Fair Oaks, CA (US); Alex Nee, Granite Bay, CA (US)

(*) Notice: Subject to any disclaimer, the term of this patent is extended or adjusted under 35 U.S.C. 154(b) by 785 days.

(21) Appl. No.: 15/597,113

(22) Filed: May 16, 2017

(65) Prior Publication Data
US 2017/0340864 A1 Nov. 30, 2017

Related U.S. Application Data

(60) Provisional application No. 62/341,018, filed on May 24, 2016.

(51) Int. Cl.
| | |
|---|---|
| *A61M 25/02* | (2006.01) |
| *A61F 5/44* | (2006.01) |
| *A61F 5/443* | (2006.01) |
| *A61F 13/00* | (2024.01) |
| *A61F 13/12* | (2006.01) |

(52) U.S. Cl.
CPC ........... *A61M 25/02* (2013.01); *A61F 5/4407* (2013.01); *A61F 5/443* (2013.01); *A61F 13/12* (2013.01); *A61F 2005/4402* (2013.01); *A61F 2013/00978* (2013.01); *A61M 2025/0266* (2013.01)

(58) Field of Classification Search
CPC ....... A61M 25/02; A61F 5/4407; A61F 5/443; A61F 2005/4402
See application file for complete search history.

(56) References Cited

U.S. PATENT DOCUMENTS

| | | | | |
|---|---|---|---|---|
| 4,360,025 | A | | 11/1982 | Edwards |
| 4,517,971 | A | | 5/1985 | Sarbonne |
| 4,723,556 | A | * | 2/1988 | Sussman ................ A61B 5/031 604/97.02 |
| 4,739,771 | A | * | 4/1988 | Manwaring ............ A61B 5/031 600/561 |
| 4,885,002 | A | * | 12/1989 | Watanabe ............... A61B 5/031 604/9 |
| 4,950,232 | A | * | 8/1990 | Ruzicka ............... A61M 27/006 604/43 |
| 4,995,856 | A | * | 2/1991 | Heindl ................ A61M 27/006 604/9 |
| 5,154,693 | A | * | 10/1992 | East .................... A61M 27/006 604/9 |
| 5,167,615 | A | * | 12/1992 | East .................... A61M 27/006 604/9 |

(Continued)

*Primary Examiner* — Guy K Townsend

(57) ABSTRACT

A ventriculostomy patch system is disclosed herein. The ventriculostomy patch system including a base-ring, and a window assembly. The base-ring includes a circular body, with the circular-body having an outer-surface, an inner-surface, a top-surface, and a bottom-surface. The bottom-surface includes a catheter-notch; the catheter-notch is configured for removably retaining a ventriculostomy catheter. The base-ring further includes at least two dome-tabs, each of the at least two dome-tabs located upon the outer surface of the base-ring. Preferably, the base-ring is constructed from anti-microbial materials. The window assembly includes an external-ring and a window, where the window assembly is removably affixable to the top-surface of the base-ring.

14 Claims, 5 Drawing Sheets

(56) References Cited

U.S. PATENT DOCUMENTS

| | | | | |
|---|---|---|---|---|
| 5,300,080 A | * | 4/1994 | Clayman | A61B 90/11 604/117 |
| 5,304,114 A | * | 4/1994 | Cosman | A61M 27/006 604/9 |
| 5,330,485 A | * | 7/1994 | Clayman | A61B 90/11 606/1 |
| 5,352,207 A | * | 10/1994 | Nussbaum | A61M 27/006 600/561 |
| 5,387,188 A | * | 2/1995 | Watson | A61M 27/006 604/8 |
| 5,531,673 A | * | 7/1996 | Helenowski | A61M 27/006 604/9 |
| 5,620,424 A | | 4/1997 | Abramson | |
| 5,637,083 A | * | 6/1997 | Bertrand | A61M 27/006 604/9 |
| 5,832,932 A | * | 11/1998 | Elsberry | A61M 5/1723 604/67 |
| 5,846,220 A | * | 12/1998 | Elsberry | A61M 25/0068 128/898 |
| 5,897,528 A | * | 4/1999 | Schultz | A61M 27/006 604/247 |
| 6,061,587 A | * | 5/2000 | Kucharczyk | A61M 31/005 604/93.01 |
| 6,193,682 B1 | * | 2/2001 | Ahmed | A61M 27/006 604/9 |
| 6,383,159 B1 | * | 5/2002 | Saul | A61M 27/006 604/9 |
| 6,453,185 B1 | * | 9/2002 | O'Keefe | A61B 5/031 600/383 |
| 6,682,508 B1 | * | 1/2004 | Meythaler | A61M 25/00 604/113 |
| 6,749,574 B2 | * | 6/2004 | O'Keefe | A61B 5/031 600/378 |
| 6,827,707 B2 | | 12/2004 | Wright et al. | |
| 6,875,192 B1 | * | 4/2005 | Saul | A61M 27/006 604/9 |
| 7,004,961 B2 | * | 2/2006 | Wong | A61F 7/123 607/104 |
| 7,014,624 B2 | * | 3/2006 | Meythaler | A61M 5/14 604/113 |
| 7,235,060 B2 | * | 6/2007 | Kraus | A61M 27/006 604/9 |
| 7,422,566 B2 | * | 9/2008 | Miethke | A61M 27/006 604/9 |
| 7,963,956 B2 | * | 6/2011 | Kunst | A61M 39/0208 604/93.01 |
| 8,328,761 B2 | * | 12/2012 | Widenhouse | A61B 17/3462 604/164.08 |
| 8,834,426 B2 | | 9/2014 | Shipman | |
| 8,870,809 B2 | * | 10/2014 | Miethke | A61M 27/006 604/9 |
| 9,039,615 B2 | * | 5/2015 | Flint | A61B 17/3423 600/129 |
| 9,168,363 B2 | * | 10/2015 | Anile | A61M 27/006 |
| 9,364,647 B1 | * | 6/2016 | Beckman | A61M 27/006 |
| 9,408,629 B2 | * | 8/2016 | Flint | A61B 90/11 |
| 9,433,764 B2 | * | 9/2016 | East | A61M 27/006 |
| 9,629,987 B2 | * | 4/2017 | Anand | A61M 39/225 |
| 9,694,166 B2 | * | 7/2017 | Hurt | A61M 25/007 |
| 9,744,338 B2 | * | 8/2017 | East | A61M 39/225 |
| 10,391,287 B1 | * | 8/2019 | Beckman | A61M 27/006 |
| 10,493,249 B2 | * | 12/2019 | East | A61M 39/225 |
| 2004/0024358 A1 | * | 2/2004 | Meythaler | A61M 27/006 604/113 |
| 2004/0138728 A1 | * | 7/2004 | Wong | A61F 7/123 607/113 |
| 2004/0215067 A1 | * | 10/2004 | Stiger | G01F 1/6845 600/300 |
| 2004/0260249 A1 | * | 12/2004 | Kulessa | A61M 27/006 604/537 |
| 2007/0083100 A1 | * | 4/2007 | Schulz-Stubner | A61B 8/445 600/463 |
| 2009/0306501 A1 | * | 12/2009 | Flint | A61B 17/3423 600/437 |
| 2010/0042070 A1 | * | 2/2010 | Gill | A61M 39/0247 604/513 |
| 2010/0081880 A1 | * | 4/2010 | Widenhouse | A61B 17/0218 600/206 |
| 2010/0081995 A1 | * | 4/2010 | Widenhouse | A61B 17/3462 600/245 |
| 2011/0282264 A1 | * | 11/2011 | Hurt | A61M 27/006 604/9 |
| 2012/0010572 A1 | | 1/2012 | Bennett | |
| 2012/0150123 A1 | * | 6/2012 | Lawrence | A61M 39/08 206/370 |
| 2012/0232462 A1 | * | 9/2012 | Miethke | A61M 39/24 604/9 |
| 2012/0302938 A1 | * | 11/2012 | Browd | A61M 39/284 604/9 |
| 2014/0207043 A1 | * | 7/2014 | Anand | A61M 25/0127 604/8 |
| 2014/0207045 A1 | * | 7/2014 | Anand | A61M 25/0127 604/9 |
| 2015/0297874 A1 | * | 10/2015 | East | A61M 39/225 604/9 |
| 2015/0367110 A1 | * | 12/2015 | East | A61M 39/225 604/9 |
| 2016/0038724 A1 | * | 2/2016 | Madsen | A61M 5/14276 604/9 |
| 2017/0189655 A1 | * | 7/2017 | Fabiano | A61M 39/0208 |
| 2017/0340864 A1 | * | 11/2017 | Rios | A61M 25/02 |

* cited by examiner

VENTRICULOSTOMY PATCH SYSTEM AND METHOD

CROSS-REFERENCE TO RELATED APPLICATION

The present application is related to and claims priority to U.S. Provisional Patent Application No. 62/341,018 filed May 24, 2016, which is incorporated by reference herein in its entirety.

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

1. Field of the Invention

The present invention relates generally to the field of medical devices, and more specifically relates to a means for securing a conduit to a body and a method for adhesion to a biological surface.

2. Description of Related Art

In the medical field, a catheter is a tube made from sterile medical grade materials that can be used in a wide variety of cases. Catheter tubes can be inserted in the body to treat diseases, perform a surgical procedure, or used post-surgery to contain drainage of body fluids. By selecting the appropriate material or providing a specific manufacturing method, it is possible to tailor catheters for cardiovascular, urological, gastrointestinal, neurovascular, and ophthalmic applications.

One such use is to drain fluid from a patient's head to relieve pressure, which may be referred to as a ventriculostomy. The current standard practice for dressing ventriculostomies is the same as for central venous catheters, in that a chlorhexidine disk is often placed around the catheter and then covered with a transparent occlusive dressing. Unfortunately, such dressings do not adhere to scalp tissue, despite the use of adjunct adhesives, but do adhere to catheters, risking dislodgement when changed, which would render the drain's lifesaving capabilities useless. Additionally, there is no seal around the site, allowing germs to invade, which can potentially lead to deadly brain infections. There is also no stabilization method for securing the catheter, other than stapling it to the scalp in multiple places, which disrupts skin integrity. A suitable solution is desired.

U.S. Pat. No. 4,360,025 to John V. Edwards relates to a catheter retainer. The described catheter retainer includes a member of synthetic plastics material having a central hole wholly or partly defined by a pair of resilient catheter-gripping jaws, and a resilient catch member for holding the jaws in their relatively closed position. The catheter retainer is preferably an insert that snaps into a coupling member which is carried by a pad of adhesive dressing material.

BRIEF SUMMARY OF THE INVENTION

In view of the foregoing disadvantages inherent in the known means for securing a conduit to a body part, the present disclosure provides a novel ventriculostomy patch system. The general purpose of the present disclosure, which will be described subsequently in greater detail, is to provide a ventriculostomy patch system and method.

A ventriculostomy patch system is disclosed herein. The ventriculostomy patch system includes a base-ring, and a window assembly. The base-ring includes a circular body, with the circular-body having an outer-surface, an inner-surface, a top-surface, and a bottom-surface. The bottom-surface includes a catheter-notch, the catheter-notch configured for removably retaining a ventriculostomy catheter. The base-ring further includes at least two dome-tabs, each of the at least two dome-tabs located upon the outer surface of the base-ring. Preferably, the base-ring is constructed from anti-microbial materials.

The window assembly includes an external-ring and a window, where the window assembly is removably affixable to the top-surface of the base-ring. Additionally, the window assembly includes a male-groove and the base-ring includes a female-groove to removably affix the window assembly to the base-ring. The window assembly is disposable and replaceable and the window assembly includes a dome which is transparent. Also, the dome is constructed from a flexible material. The window assembly further includes a window-tab located on the periphery of the window. The window assembly is constructed from anti-microbial materials.

The interface between the male-groove of the window assembly and the female-groove of the base-ring includes a gasket configured to provide a sterile seal from external elements.

Preferably the bottom-surface of the base-ring includes a recessed-groove, and the bottom-surface of the base-ring includes a semi-liquid adhesive gel contained within the recessed-groove and affixable to the scalp of a user. The adhesive-ring is covered by a removable backing and the adhesive-ring is constructed from an anti-bacterial material. Also, the recessed-groove of the bottom-surface of the base-ring may include at least one clip configured for holding and retaining the ventriculostomy catheter.

According to another embodiment, a method of using a ventriculostomy patch system is also disclosed herein. The method of using a ventriculostomy patch system includes: a first step, removing a backing from the ventriculostomy patch system; a second step, placing the ventriculostomy patch system over a ventriculostomy catheter (by snapping a catheter into a recessed groove) and adhering the base-ring to scalp; a third step, placing the window assembly over the base-ring by snapping the male groove of the window assembly into female groove of base-ring; a fourth step, when dressing is changed, window assembly can be changed by pulling window tab to remove the old (i.e. used, soiled, contaminated, etc . . . ) window assembly while leaving the base-ring in place, then placing a new window assembly over the base-ring (similar to as described in step three above). All steps above are to be completed using sterile technique and adjunct biological surface cleansing products contained in sterile packaging with the separate pieces of the ventriculostomy patch system.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a ventriculostomy patch system and method, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to a means for securing a conduit to a body and more particularly a method of adhesion to a biological surface as used to improve the prevention of infection during a ventriculostomy catheter usage while additionally securing the catheter to a scalp of a user.

Generally, the ventriculostomy patch system provides a sterile, changeable dressing for ventriculostomy catheters with two main purposes: a bacteriostatic covering to prevent infection, and additional catheter securement capabilities. This dressing is designed for neurosurgical/neurointensive care patients who require ventriculostomy placement for drainage of cerebrospinal fluid and/or monitoring of intracranial pressures. The ventriculostomy patch system is intended for use in the operating room, an intensive care unit, or Neuro step-down unit where ventriculostomies are initially placed and patients with these catheters are cared for over periods of time.

This surgical dressing for ventriculostomies (brain drains) may come in two packages: the base pack, and a change pack. The base pack may include a gasket-like foam or silicone ring that has a track on the bottom (touching the scalp) containing a gel adhesive that will be released as a backing is peeled away. The ring will have a flexible plastic track on the underside which the ventriculostomy catheter will snap into as the dressing is placed. The top of the base (facing upward) will have grooves designed for the window of the change pack to snap into it. Also in the base pack may be a Betadine or Chlorhexidine cleanser, skin prep or benzoin tincture, sterile gloves, mask and gauze. The change pack is used to complete the dressing and will include a second flexible plastic frame window with a clear plastic lens that will snap into the frame of the base gasket after the previous window assembly has been discarded.

Figure 1:
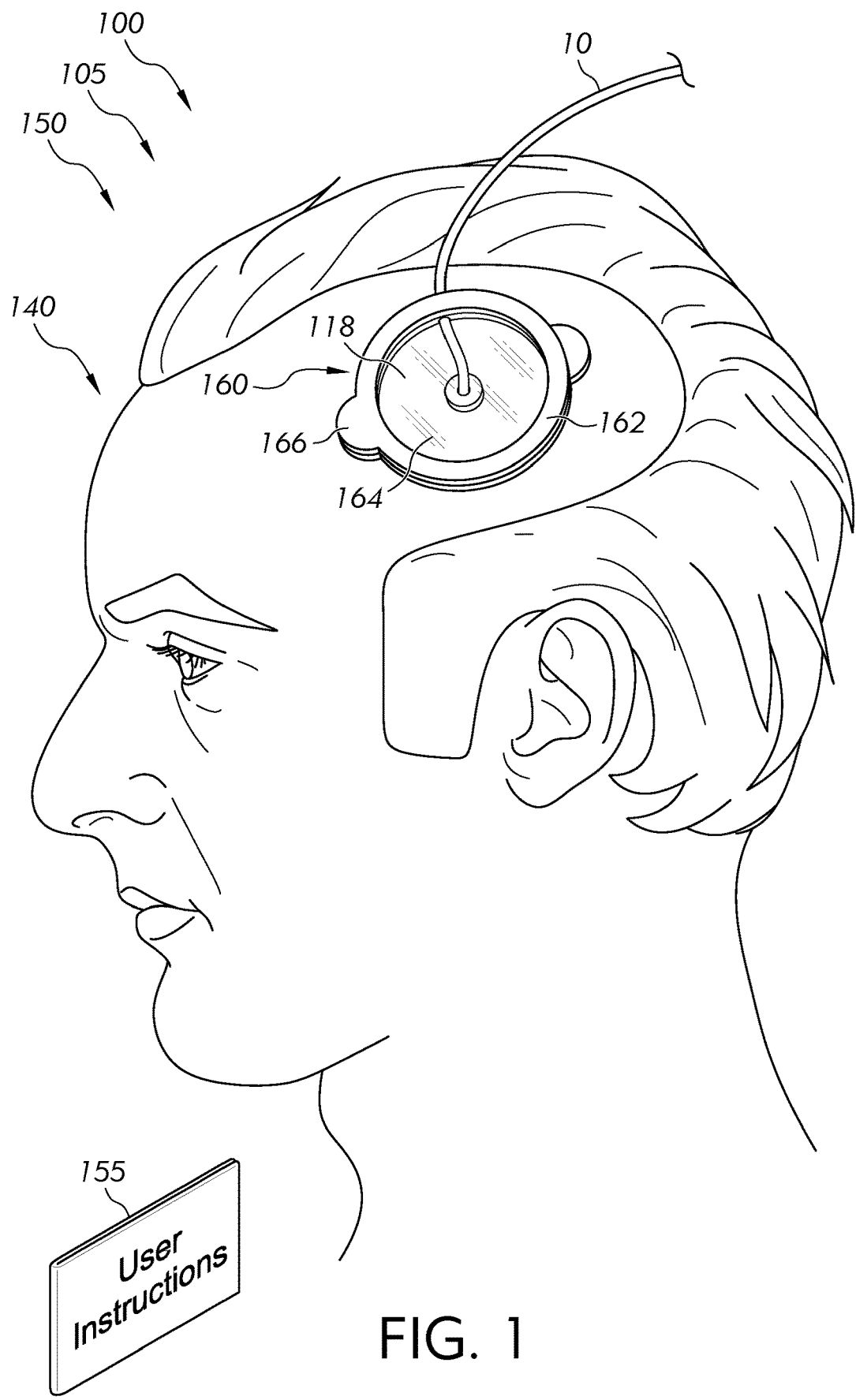
FIG. 1 is a perspective view of the ventriculostomy patch system during an 'in-use' condition, according to an embodiment of the disclosure.

Referring now more specifically to the drawings by numerals of reference, there is shown in FIGS. 1-4, various views of ventriculostomy patch system 100. FIG. 1 shows a ventriculostomy patch system 100 during an 'in-use' condition 150, according to an embodiment of the present disclosure. Here, ventriculostomy patch system 100 may be beneficial for use by a user 140 to provide a sterile barrier against infection to a ventriculostomy site as well as providing additional securement to catheter 10. As illustrated, the ventriculostomy patch system 100 may include base-ring and window-assembly 160.

Figure 2:
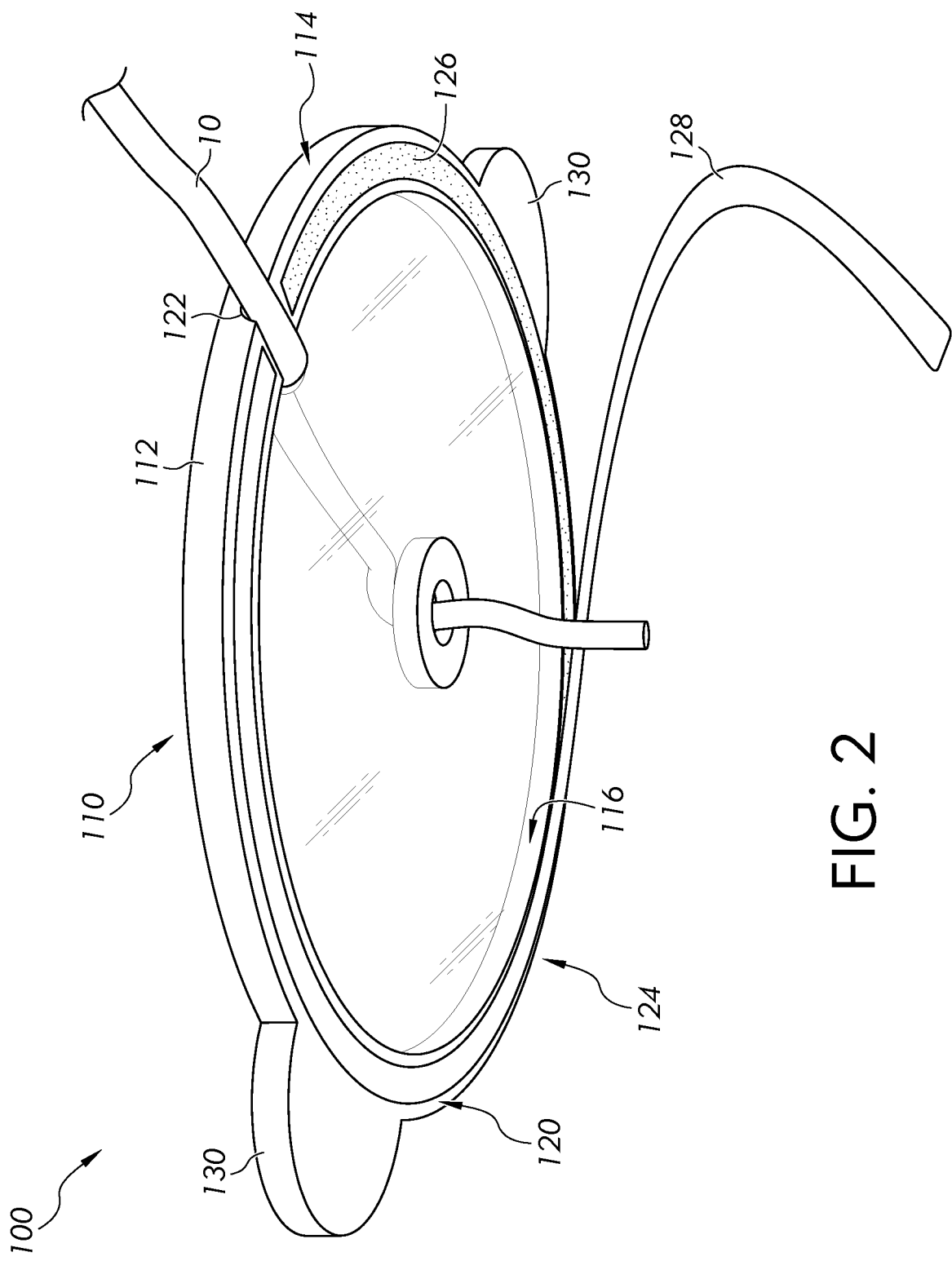
FIG. 2 is a perspective view of the base-ring of the ventriculostomy patch system of FIG. 1, according to an embodiment of the present disclosure.

Base-ring 110 may include circular body 112, where circular-body may have outer-surface 114, inner-surface 116, top-surface 118 and bottom-surface 120, with bottom-surface including catheter-notch 122 in embodiments (as shown in FIG. 2). Embodiments may include base-ring constructed from anti-microbial materials.

Window assembly 160 may include external-ring 162 and window 164, where window assembly 160 may be removably affixable to top-surface of base-ring. Window assembly may additionally include window-tab 166 located on the periphery of window 164, window assembly is disposable and replaceable, in embodiments. Additional embodiments may include window assembly 160 which includes window 164 which is transparent, and/or window 164 constructed from a flexible material. In some additional embodiments window 164 may be opaque. Window may be constructed in many shapes and forms (e.g., dome-shaped, flat, etc.) as well as colors and/or textures. Window assembly 160, and/or its components may be constructed from anti-microbial materials.

According to one embodiment, the ventriculostomy patch system 100 may be arranged as a kit 105. In particular, the ventriculostomy patch system 100 may further include a set of instructions 155. The instructions 155 may detail functional relationships in relation to the structure of the ventriculostomy patch system 100 (such that the ventriculostomy patch system 100 can be used, maintained, or the like, in a preferred manner).

Figure 4:
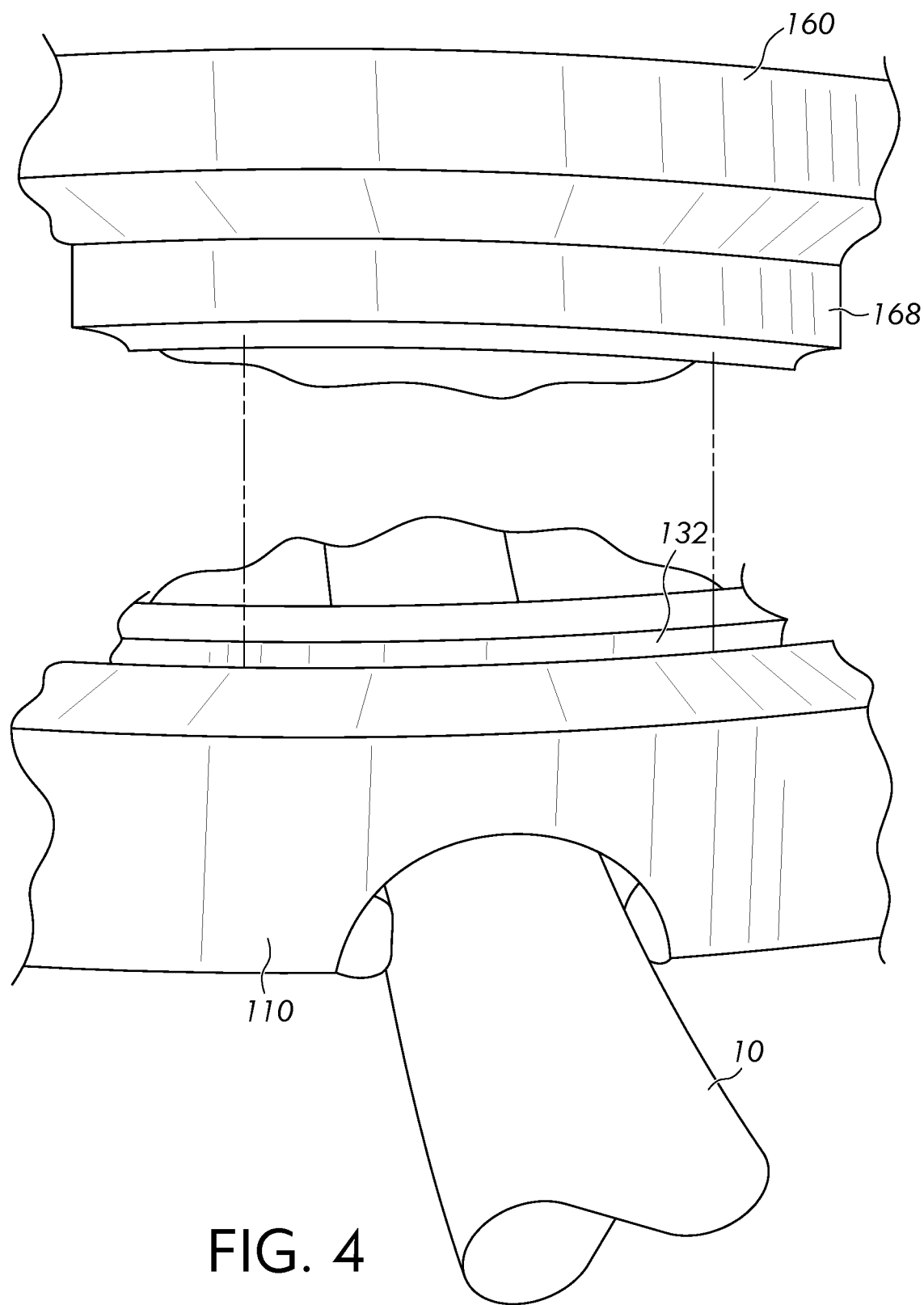
FIG. 4 is a detail view of the ventriculostomy patch system of FIGS. 1-3, according to an embodiment of the present disclosure.

FIG. 2 shows the ventriculostomy patch system 100 of FIG. 1, according to an embodiment of the present disclosure. As above, the ventriculostomy patch system 100 may include base-ring. Base-ring 110 may include circular body 112, where circular-body 112 may include outer-surface 114, inner-surface 116, top-surface 118 (as can be seen in FIG. 4), and bottom-surface 120, where bottom-surface 120 may include catheter-notch 122. Catheter-notch 122 of bottom-surface 120 of base-ring 110 may be configured for removably retaining a ventriculostomy catheter 10.

Bottom-surface 120 of base-ring 110 may additionally include recessed-groove 124, and bottom-surface 120 of base-ring 110 may also include adhesive-ring 126 contained within recessed-groove and affixable to a scalp of user 140 (user 140 shown in FIG. 1). Adhesive-gel ring 126 may be covered by a removable backing 128, to protect adhesive-gel ring 126 during storage and transport prior to use. Adhesive-gel ring 126 may also be constructed from an anti-bacterial material. Base-ring 110 may further include at least two dome-tabs 130, each of at least two dome-tabs 130 located upon outer surface 114 of base-ring 110.

Figure 3:
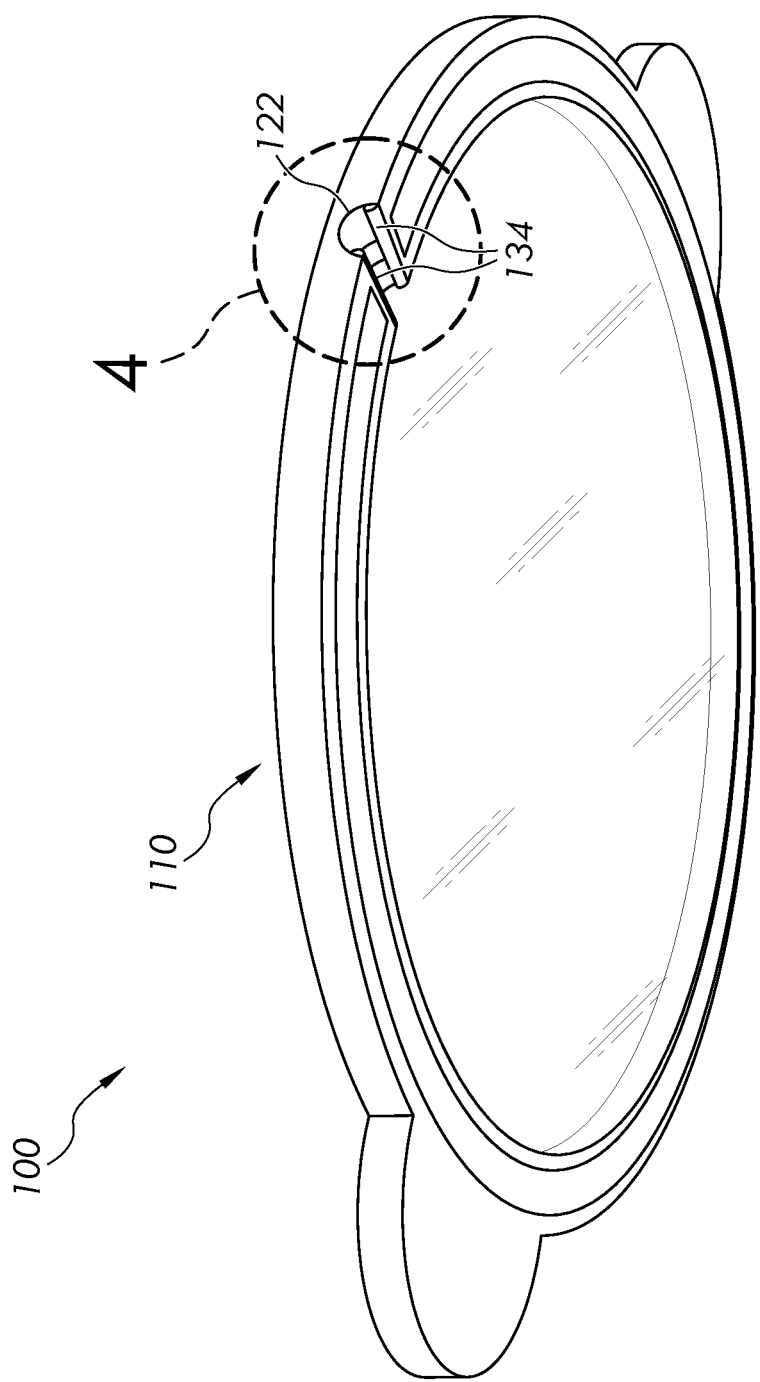
FIG. 3 is an additional perspective view of the base-ring of the ventriculostomy patch system of FIGS. 1-2, according to an embodiment of the present disclosure.

FIG. 3 is a perspective view of the base-ring of the ventriculostomy patch system 100 of FIG. 1, according to an embodiment of the present disclosure. Recessed-groove 124 of bottom-surface 120 of base-ring 110 may include at least one clip 134 located in catheter-notch 122, configured for holding and retaining ventriculostomy catheter 10.

FIG. 4 is a detailed view of the ventriculostomy patch system of FIG. 1, according to an embodiment of the present disclosure. As shown, window assembly 160 may include male-groove 168, and base-ring 110 may include female-groove 132 to removably affix window assembly 160 to base-ring 110.

Figure 5:
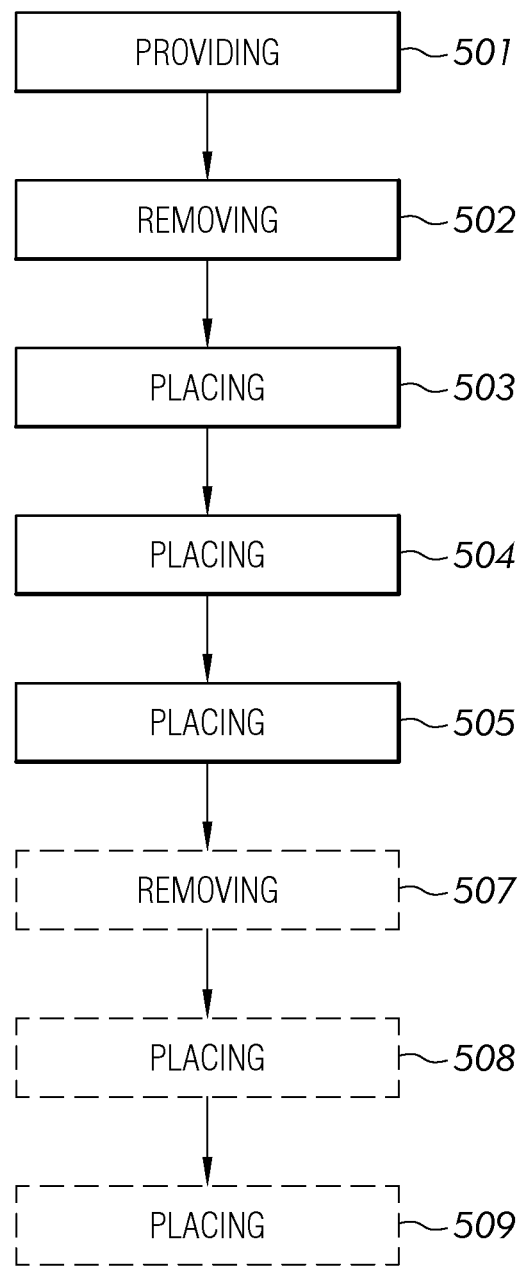
FIG. 5 is a flow diagram illustrating a method of using the ventriculostomy patch system, according to an embodiment of the present disclosure.

FIG. 5 is a flow diagram illustrating a method of using a ventriculostomy patch system, according to an embodiment of the present disclosure. In particular, the method of using a ventriculostomy patch system 500 may include one or more components or features of the ventriculostomy patch system 100 as described above. As illustrated, the method of using a ventriculostomy patch system 500 may include the steps of: step one 501, removing backing from ventriculostomy patch system 100; step two 502, placing ventriculostomy patch system 100 over ventriculostomy catheter 10 (snapping catheter into recessed groove 124) and adhering base-ring 110 to a scalp; step three 503, placing window assembly 160 over base-ring 110 by snapping male groove 168 of window assembly 160 into female groove 132 of base-ring 110; step four 504, changing a dressing, when the dressing is changed, window assembly 160 can be changed by pulling window tab 166 to remove old window assembly 160 while leaving base-ring 110 in place, then placing new window assembly 160 (as described in step three above).

It should be noted that step four 504, and step five 505 are optional steps and may not be implemented in all cases. Optional steps of method of use 500 are illustrated using dotted lines in FIG. 5 so as to distinguish them from the other steps of method of use 500. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other method of using a ventriculostomy patch system (e.g., different step orders within above-mentioned list, elimination or addition of certain steps, including or excluding certain maintenance steps, etc.), are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A ventriculostomy patch system for placing a catheter on a scalp of a user, the system comprising:
    a base defined by a body including:
        an aperture through the body defining an enclosed area,
        an inner surface wall defining boundaries of the enclosed area of the aperture,
        an outer surface wall surrounding the inner surface wall, the outer surface wall defining outer boundaries of the body,
        a bottom surface extending between the inner surface wall and the outer surface wall,
        a top surface extending between the inner surface wall and the outer surface wall, the top surface disposed opposite the bottom surface, and
        a notch that extends across a portion of the bottom surface, the notch extending through the inner surface wall and the outer surface wall, and the notch being sized to removably retain the catheter upon use of the system, where the use of the system includes placement of the catheter under the base on the scalp of the user, such that the bottom surface abuts the scalp on lateral sides of the catheter to retain the catheter in position against the scalp during the use of the system; and
    a window assembly that is removably affixable to the top surface of the base to provide a cover over the enclosed area of the base, the window assembly including:
        a frame defining boundaries of a viewing area, the frame being sized to cover the enclosed area of the base, and
        a transparent window spanning the viewing area.

2. The ventriculostomy patch system of claim 1, wherein the base further includes a recessed-groove that extends along the bottom surface of the body up to adjacent sides of the notch.

3. The ventriculostomy patch system of claim 2, wherein the body further includes an adhesive-gel ring contained within said recessed-groove to adhere the base to the scalp of the user.

4. The ventriculostomy patch system of claim 2, wherein the notch includes at least two clips that extends along a length of the notch, the clip being configured for holding and retaining the catheter.

5. The ventriculostomy patch system of claim 1, further comprising an adhesive-ring disposed on the bottom surface of the body of the base, and wherein the adhesive-ring is covered by a removable backing before the use.

6. The ventriculostomy patch system of claim 1, wherein the base includes an anti-microbial material.

7. The ventriculostomy patch system of claim 6, wherein the base further includes anti-bacterial material.

8. The ventriculostomy patch system of claim 7, wherein said dome is constructed from a flexible material.

9. The ventriculostomy patch system of claim 1, wherein the frame includes a window-tab located on a periphery thereof.

10. The ventriculostomy patch system of claim 1, wherein the base includes one or more tabs.

11. The ventriculostomy patch system of claim 1, wherein the window assembly includes anti-microbial materials.

12. The ventriculostomy patch system of claim 1, further comprising a set of instructions; and
    wherein the system is arranged as a kit.

13. The ventriculostomy patch system of claim 1, wherein the window assembly further includes anti-bacterial materials.

14. A ventriculostomy patch system for placing a catheter on a scalp of a user, the system comprising:
    a first component; and
    a second component configured to attach and detach from the first component,
    wherein the first component is configured to be placed on the scalp of the user, and wherein the first component includes a body including:
an aperture through the body defining an enclosed area,
an inner surface wall defining boundaries of the enclosed area of the aperture,
an outer surface wall surrounding the inner surface wall, the outer surface wall defining outer boundaries of the body,
a bottom surface extending between the inner surface wall and the outer surface wall,
a top surface extending between the inner surface wall and the outer surface wall, the top surface disposed opposite the bottom surface, and
a notch that extends across a portion of the bottom surface, the notch extending through the inner surface wall and the outer surface wall, and the notch being sized to removably retain the catheter upon use of the system, where the use of the system includes placement of the catheter under the first component on the scalp of the user, such that the bottom surface abuts the scalp on lateral sides of the catheter to retain the catheter in position against the scalp during the use of the system, and wherein the second component includes a window assembly that is removably affixable to the top surface of the first component to provide a cover over the enclosed area of the first component, the window assembly including:
a frame defining boundaries of a viewing area, the frame being sized to cover the enclosed area of the first component, and
a window spanning the viewing area.

\* \* \* \* \*